US007141990B2

(12) United States Patent
Bast et al.

(10) Patent No.: US 7,141,990 B2
(45) Date of Patent: Nov. 28, 2006

(54) DEVICE FOR DETECTING DEGRADATION OF A COMPONENT

(75) Inventors: Ulrich Bast, München (DE); Stefan Lampenscherf, Oberschleissheim (DE); Uwe Rettig, München (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 10/516,084

(22) PCT Filed: May 22, 2003

(86) PCT No.: PCT/DE03/01658

§ 371 (c)(1), (2), (4) Date: Nov. 29, 2004

(87) PCT Pub. No.: WO03/102567

PCT Pub. Date: Dec. 11, 2003

(65) Prior Publication Data

US 2005/0212535 A1 Sep. 29, 2005

(30) Foreign Application Priority Data

May 29, 2002 (DE) ................................ 102 23 985

(51) Int. Cl.
*G01R 27/08* (2006.01)
*G01N 19/08* (2006.01)

(52) U.S. Cl. ........................................ 324/708; 73/799

(58) Field of Classification Search ................ 324/708, 324/707, 691, 649, 600, 663, 263, 378, 537; 73/104, 762, 799
See application file for complete search history.

(56) References Cited

U.S. PATENT DOCUMENTS 4,026,660 A 5/1977 Ueda et al.
4,255,974 A * 3/1981 Dufrane et al. ............... 73/776
4,484,132 A * 11/1984 Crites ......................... 324/557
4,914,378 A * 4/1990 Hayashi et al. ............ 324/696
5,355,734 A * 10/1994 Kajino ........................ 73/775
5,647,667 A * 7/1997 Bast et al. .................... 374/57
6,532,810 B1 * 3/2003 Ahmed ..................... 73/119 R
6,686,750 B1 * 2/2004 Watanabe et al. ........... 324/691
6,911,828 B1 * 6/2005 Brossia et al. .............. 324/649

FOREIGN PATENT DOCUMENTS

| | | |
|---|---|---|
| DE | 36 36 321 A1 | 4/1988 |
| DE | 44 19 750 C1 | 6/1995 |
| DE | 198 10 674 A1 | 10/1998 |
| DE | 199 23 143 A1 | 11/2000 |
| DE | 100 46 094 A1 | 5/2002 |
| EP | 0 217 242 A2 | 4/1987 |
| EP | 0 685 297 A1 | 12/1995 |
| JP | 06118618 A | 4/1994 |

* cited by examiner

*Primary Examiner*—Anjan Deb
*Assistant Examiner*—Hoai-An D. Nguyen

(57) ABSTRACT

An apparatus for monitoring the structural integrity of a component. A monitoring structure is applied to a component that is subject to structural degradation. The monitoring structure includes an electrical conductor that becomes cracked if the component becomes structurally degraded. When the component is a ductile metal component that may be degraded by bending, the electrical conductor is formed of a brittle material that cracks when the ductile metal component is bent. When the component is a brittle ceramic heat shield wherein a crack having a critical length is of concern, the electrical conductor is located at a predetermined location wherein a critical length crack in the component will propagate into the conductor. A crack in the electrical conductor is detected with a monitoring device to indicate a degraded structural condition in the component.

5 Claims, 2 Drawing Sheets

16
15
14
11
12
14
5
15
2,10
16
16
5
1

Arrange component and monitoring structure against one another
41
Fixedly connect the component and the monitoring structure
42

Determine the actual value of the electrical property of the monitoring structure
51
Compare the actual value with the desired value for the electrical property of the monitoring structure
52

DEVICE FOR DETECTING DEGRADATION OF A COMPONENT

CROSS REFERENCE TO RELATED APPLICATION

This application is the US National Stage of International Application No. PCT/DE03/01658, filed May 22, 2003 and claims the benefit thereof. The International Application claims the benefits of German application No. 10223958.1 DE filed May 29, 2002, both of the applications are incorporated by reference herein in their entirety.

FIELD OF THE INVENTION

The invention relates to an arrangement comprising a component and at least one monitoring device for recording degradation of the component. The invention also provides a process for producing the arrangement and a method for checking the ability of the component to function using the arrangement.

BACKGROUND OF THE INVENTION

DE 36 36 321 A1 shows an arrangement and a method for determining the state of wear of a component.

An arrangement of the abovementioned type is known, for example, in the context of a combustion chamber of a gas turbine. The combustion chamber has an interior space and a housing surrounding the interior space. A fossil fuel is burnt in the interior space of the combustion chamber. A temperature of up to 1500° C. is reached during the combustion. Corrosive gases are also produced and attack the housing of the combustion chamber. To protect the housing from the high temperatures and from attack from corrosive gases, the combustion chamber is lined with a large number of what are known as ceramic heat shields.

A heat shield is a component formed from a component material which has a very good resistance to temperature and corrosion. The component material is, for example, a ceramic material in the form of mullite. On account of a porous structure with a multiplicity of microcracks, the ceramic material has very good thermal shock properties. A very strong temperature fluctuation, as occurs, for example, in the combustion chamber of the gas turbine when the combustion process is interrupted, is compensated for without the heat shield being destroyed. However, in the event of a mechanical overload of the heat shield, the heat shield can be degraded. A crack (macrocrack) can form in the heat shield. A crack of this nature forms in particular at an edge of the heat shield. In operation, the crack can propagate toward the center of the heat shield. Up to a certain length, the crack has no adverse effect on the ability of the heat shield to function and can therefore be tolerated. However, if the crack exceeds a defined length, the ability of the heat shield to function is no longer ensured. It is necessary to replace the heat shield in order to avoid fracture of the heat shield caused by the crack while the gas turbine is operating. It is therefore absolutely imperative that the existence of a crack be detected and that the length of the crack be determined.

The recording of the crack or the length of the crack in the heat shield is carried out during a stationary phase of the gas turbine with the aid of an inspection device for optical recording of the crack. The recording is generally carried out from the interior space of the combustion chamber. An optically accessible surface portion of the heat shield which faces the interior space of the combustion chamber is inspected. On the other hand, if the rear surface of the heat shield is to be inspected, this can often only be done by dismantling the heat shield. The rear surface is a surface portion of the heat shield which is remote from the interior space of the combustion chamber. The method which has been demonstrated for recording the degradation and therefore for checking the ability of the heat shield to function is very time-consuming and therefore expensive.

SUMMARY OF THE INVENTION

It is an object of the invention to show how degradation of a component can be recorded simply, quickly and reliably.

To achieve the object, the invention provides an arrangement comprising a component and at least one monitoring device for recording degradation of the component.

The arrangement is characterized in that the monitoring device having at least one electrically conductive monitoring structure which is decoupled from a function of the component and has a defined electrical property, and the component and the monitoring structure are fixedly connected to one another in such a manner that the degradation of the component causes degradation of the monitoring structure and therefore a change in the defined electrical property of the monitoring structure. Moreover, there is no permanent electrical connection or permanent electromagnetic coupling.

To achieve the object, the invention also provides a process for producing the arrangement, comprising the following process steps:

a) arranging the component and the monitoring structure against one another, and
b) fixedly connecting the component and the monitoring structure,
c) providing a monitoring device (3) which is not permanently electrically or electromagnetically connected to the monitoring device (4).

Furthermore, to achieve the object, the invention proposes a method for checking the ability of a component to function using the arrangement. The method for checking the ability of the component to function comprises the following method steps:

a) determining an actual value of at least one defined electrical property of the monitoring structure with an electrical or electromagnetic coupling being produced between monitoring structure (4) and monitoring device (3),
b) comparing the actual value of the electrical property with a desired value, representing the ability of the component to function, of the electrical property.

The electrically conductive monitoring structure is any desired structured network of resistances, capacitances and inductances. The size, shape and conductor material of the monitoring structure and the fixed connection between the monitoring structure and the component are selected in such a manner that the degradation of the component continues as a degradation of the monitoring structure. The degradation of the monitoring structure leads to a change in the electrical property of the monitoring structure. This change is recorded by comparing the actual value and desired value of the electrical property of the monitoring structure. The determination of the electrical properties of the monitoring structure allows checking of a state of the component and therefore checking of the ability of the component to function.

To check the state of the component, the monitoring structure is, for example, applied to a critical location of the component. The occurrence of the degradation of the component at the critical location means that the ability of the component to function would only be ensured to a restricted extent or even would no longer be ensured at all.

The component is, for example, a heat shield as described in the introduction. The ability of the heat shield to function is only ensured if a crack which propagates from the edge of the heat shield toward the center of the heat shield does not exceed a defined critical length. In this example, the critical location of the heat shield would be defined by a specific distance from the edge of the heat shield toward the center of the heat shield. The monitoring structure is arranged on the surface of the heat shield at this distance, for example in the shape of a ring, around the center of the heat shield.

The described arrangement of heat shield and monitoring device can advantageously also be used to check for the presence of the heat shield in the combustion chamber. If the monitoring structure delivers a corresponding signal, the heat shield is present. The ability of the heat shield to function is ensured. If, on the other hand, a corresponding signal cannot be detected, either the degradation of the heat shield has advanced to such an extent that the monitoring structure has been destroyed, or the heat shield with the monitoring structure is no longer present. In both cases, the ability of the heat shield to function is no longer ensured. Continuous checking during an operating phase of the heat shield or the combustion chamber having the heat shield makes it possible to react to the degradation or absence of the heat shield very quickly. Subsequent damage associated with the degradation or absence of the heat shield can be restricted to a considerable degree.

In one particular configuration, the degradation of the component and/or the degradation of the monitoring structure is selected from the group consisting of deformation and/or removal of material and/or crack formation and/or crack propagation. By way of example, bending occurs as deformation of the component. If the monitoring structure connected to the component consists of a brittle, electrically conductive material, the bending of the component can lead to a crack or fracture of the monitoring structure. This would, for example, change an electrical DC resistance of the monitoring structure. The bending is detected by comparing the actual value of the electrical DC resistance of the monitoring structure with the desired value of the electrical DC resistance. The bending can be recorded even without the component being directly accessible.

In one particular configuration, the monitoring structure has at least one electrical resonant circuit. In particular, the defined electrical property of the monitoring structure is selected from the group consisting of DC resistance and/or impedance and/or radiofrequency resonance property. Therefore, there are various options for recording the degradation of the component. The methods described can be carried out individually or in combination with one another.

The degradation is recorded, for example, by a resonance measurement. This is possible with a monitoring structure in the form of a resonant circuit. The resonant circuit acts as a resonator for a radiofrequency signal. The radiofrequency signal can be introduced into the resonant circuit with the aid of an antenna. The radiofrequency signal is emitted again by the resonant circuit and can be recorded by the same antenna or a different antenna. Damage to an interconnect in the resonant circuit leads to a change in the resonance property in terms of a frequency and/or amplitude and/or phase of the radiofrequency signal. It is in this way possible in particular to record degradation of an inaccessible surface portion of a component. The possibility of recording the degradation is in this case not restricted by the thickness of the heat shields. To record the degradation, the component merely needs to be scanned by the antenna. By way of example, a resonant circuit is arranged on the rear side of the heat shield of a combustion chamber, which is not accessible in the installed state. A crack is recorded in a stationary phase of the gas turbine by simply placing the antenna onto the heat shield in the interior space of the combustion chamber. In this way, the ability of a large number of heat shields to function can be checked within a very short time.

Alternatively, it is also possible to measure the DC resistance. Partial or complete interruption of an interconnect of the monitoring structure leads to a change in the DC resistance of the monitoring structure. By way of example, the component has an electrical via for the electrical contact-connection of a monitoring structure which is not accessible. The DC resistance of the monitoring structure can be measured using the via. In the case of a heat shield installed in the combustion chamber, the DC resistance can be measured, for example, by the monitoring structure being electrically contact-connected through a gap between adjacent heat shields.

An impedance measurement can also be carried out to check the ability of the component to function. In this case, a frequency-dependent impedance of the monitoring structure is measured. The impedance likewise changes if the interconnect of the monitoring structure is damaged. The electrical contact connection is carried out in the same way as for the resistance measurement.

A combination of the three measurement methods described is advantageous for determining the ability of the monitoring structure to function. It is possible to check a minimum function of the monitoring structure.

In one particular configuration, the monitoring structure includes at least one electrically conductive conductor material selected from the group consisting of metallic conductors and/or ceramic conductors. By way of example, it is conceivable for the monitoring structure to be composed of what is known as a cermet. In the cermet, particles of a metallic conductor are distributed in a ceramic in such a manner that a defined electrical conductivity results. Alternatively, the monitoring structure may consist of an electrically conductive, ceramic material. In both cases, a brittle conductor material is present. A crack in the component may continue as a crack in the monitoring structure.

The component material of the component and the conductor material of the monitoring structure may consist of completely different materials with different mechanical properties. By way of example, the component consists of a metal. On account of a ductility of the metal, degradation of the component may occur in the form of bending. To enable the bending to be determined with the aid of the monitoring structure, by way of example the monitoring structure is applied to the surface of the component in an electrically insulating manner. By way of example, a ceramic functions as electrical insulator. If the monitoring structure is formed from a brittle conductor material, the bending of the component leads to a crack in the monitoring structure. An electrical property of the monitoring structure changes. Consequently, the bending of the component can be detected.

In one particular configuration, a component material of the component and the conductor material of the monitoring structure have a substantially identical mechanical property. This mechanical property is selected in particular from the group consisting of thermal expansion behavior and fracture toughness. In the case of a component in the form of a heat shield, there is a very great difference in temperature between an operating phase and a stationary phase of the gas turbine. In operation, a temperature of up to 1500° C. is reached, for example, in the interior space of the combustion chamber. The substantially identical temperature expansion behavior ensures that the contact between the monitoring structure and the component continues even during a change between operating phase and stationary phase. It is particularly advantageous if the fracture toughness of the component material and the conductor material are substantially identical. In particular, this has the result that a fracture or crack in the component can continue into the monitoring structure.

In addition to the substantially identical mechanical properties, it is advantageous if the component material and the conductor material are distinguished by an at least similar stability with respect to an external influence. The external influence is, for example, an atmosphere or a temperature to which the component and/or the monitoring structure are exposed during operation. By way of example, when the combustion chamber is operating, a surface temperature of up to 800° C. occurs on the surface portion of the heat shield which is remote from the interior space. Therefore, the conductor material of the monitoring structure is advantageously able to withstand temperatures of up to 800° C.

In a further configuration, the monitoring structure is arranged at a surface portion of the component and/or in the volume of the component. To produce the arrangement, by way of example, a ceramic material is used as component material of the component and/or as conductor material of the monitoring structure. Joint sintering of the component and the monitoring structure is carried out to fixedly connect the component and the monitoring structure. By way of example, a paste of a ceramic conductor material is applied to the surface portion of a ceramic component which is already complete. The surface portion may in this case be formed by a groove located in the component, in the shape of the monitoring structure that is to be produced. By way of example, a screen-printing process or a mask process is suitable for applying the paste. The conductor material is in this case applied as a loop, spiral or meandering structure, depending on the particular requirements. The crucial factors in this context are the nature, shape and tolerance limit of the degradation that is to be recorded. As a result of joint sintering at a sintering temperature of the paste, the monitoring structure comprising the ceramic conductor material is then formed from the paste. It is also conceivable for the component to be in the form of a ceramic green body and for the paste of the ceramic conductor material to be applied to the ceramic green body. The arrangement is produced by joint sintering which both densifies the ceramic component material of the component and densifies the ceramic conductor material of the monitoring structure.

In a further configuration of the invention, the monitoring structure is arranged in the volume of the component. This is achieved, for example, by the component comprising a plurality of layers. The layers are joined together with the monitoring structure, for example by joint sintering. The result is a multilayer ceramic body with the monitoring structure integrated in its volume. Any electrical contact connection which may be required for impedance or resistance measurement is advantageously effected by means of an electrical via.

To summarize, the invention results in the following particular advantages:

- the present invention allows a fast, simple and nondestructive testing method for recording degradation of a component.
- The component itself may have an extremely inhomogeneous structure. The component may also have a relatively great component thickness. It is possible to detect the degradation even under these boundary conditions.
- The degradation can be determined even at a surface portion of the component which is relatively inaccessible.
- The ability of the component to function can be determined both in a stationary phase and in an operating phase.
- The ability of the component to function is checked in a simple, fast and reliable way.

BRIEF DESCRIPTION OF THE DRAWINGS

The invention is presented in more detail in the text which follows on the basis of a plurality of exemplary embodiments and the associated figures. The figures are diagrammatic and constitute illustrations which are not to scale.

DETAILED DESCRIPTION OF THE INVENTION

EXAMPLE 1

Figure 2:
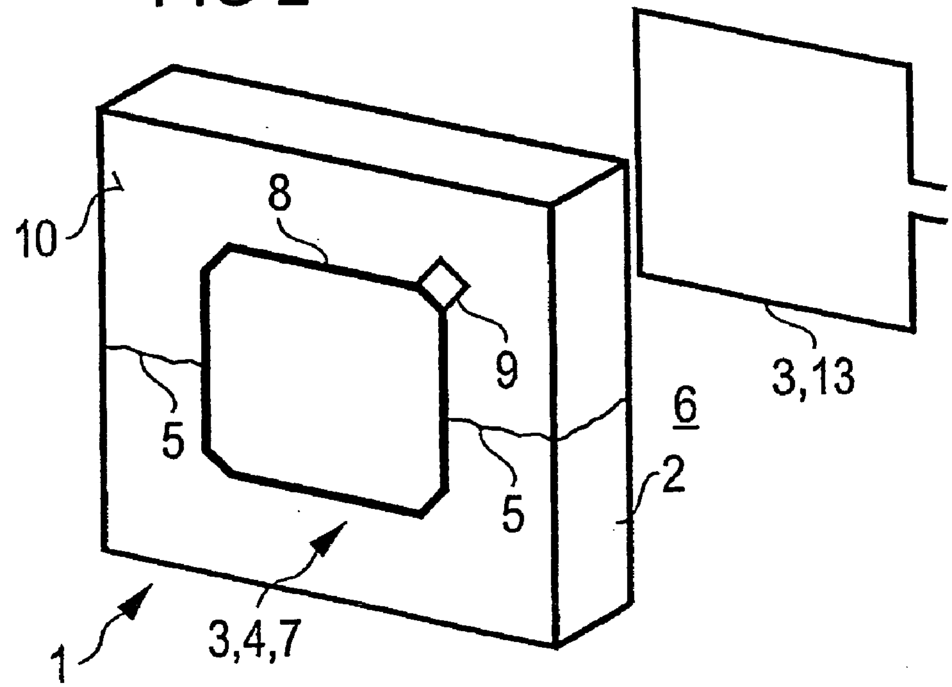
FIG. 2 shows an arrangement comprising component and monitoring device with monitoring structure in the form of a perspective illustration.
Figure 3:
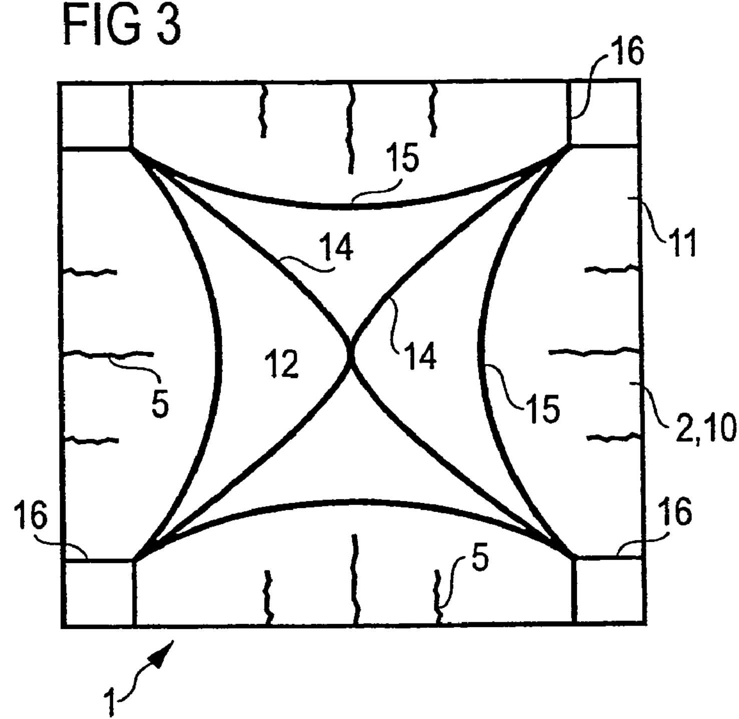
FIG. 3 shows a monitoring structure applied to a surface portion of the component.

The arrangement 1 comprises a component 2 in the form of a heat shield and a monitoring device 3 for recording degradation 5 of the component 1 (FIG. 2). The monitoring device 3 has an electrically conductive monitoring structure 4 with a defined electrical property applied to a surface portion 10 of the heat shield 1. The monitoring device 3 and the monitoring structure 4 are not permanently electrically connected to one another.

The surface portion 10 is, for example, remote from the interior space 6 of a combustion chamber. The monitoring structure is a resonant circuit 7 comprising an interconnect 8 and a capacitor 9. The degradation 5 that is to be recorded is a propagation of an existing crack.

The heat shield 2 includes a ceramic as component material. The ceramic is mullite. The conductor material of the monitoring structure 4 is an electrically conductive ceramic conductor which is able to withstand temperatures of up to 800° C. The conductor material and the component material are brittle. They have substantially the same fracture toughness.

Figure 1:
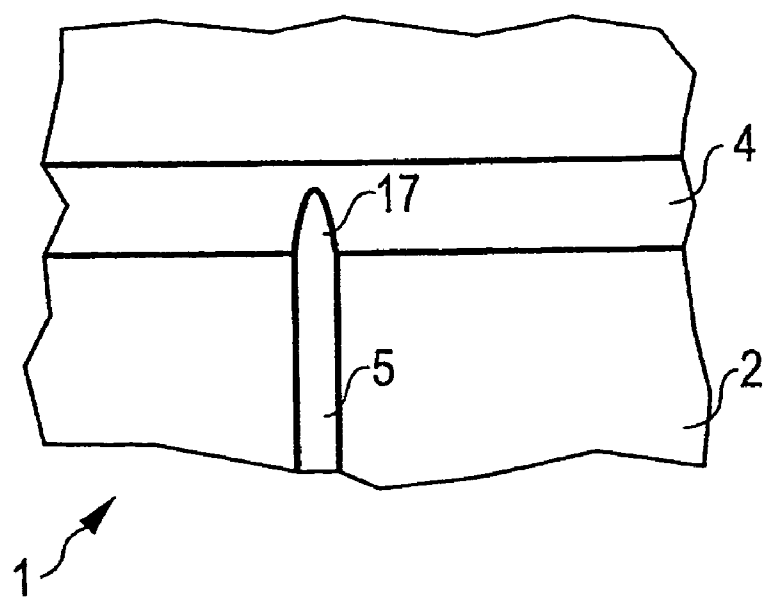
FIG. 1 shows a degradation of a component which continues as a degradation of the monitoring structure.

The monitoring structure 4 has been applied to the surface portion 10 of the heat shield 2 in such a manner that each crack 5 in the heat shield 2 which propagates from the edge 11 of the heat shield 2 toward the center 12 of the heat shield 2 and exceeds a defined length continues into the monitoring structure 4. As soon as the length of the crack 5 exceeds a critical length, further propagation of the crack 5 leads to degradation 17 (crack formation) in the monitoring structure 4 (FIG. 1). The electrical properties of the monitoring structure 4 change.

To record the degradation of the control structure 4 and therefore to record the degradation 5 of the heat shield 2, energy in the form of a radiofrequency signal is introduced (electromagnetically) into the resonant circuit 7 with the aid of an antenna 13. In this case too, there is no need for a direct electrical connection (fixed cable connection) of monitoring structure 4 and monitoring device 3, since electromagnetic coupling is effected.

If the monitoring structure 4 is destroyed, the energy cannot be introduced into the monitoring structure 4. The degradation of the monitoring structure 4 is recorded by the antenna 13, which functions not only as an emitter but also as a receiver of the radiofrequency resonant signal, on account of the fact that the monitoring structure 4 does not emit any energy that can be picked up by the antenna 13.

Figure 5:
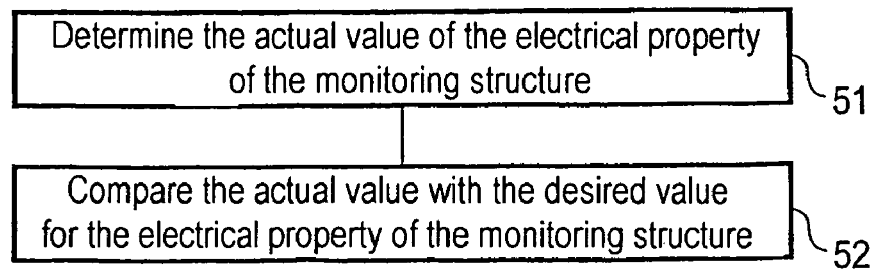
FIG. 5 shows a method for checking an ability of a component to function using the arrangement.

To record the ability of the heat shield 2, which is installed in a combustion chamber of a gas turbine, to function, the radiofrequency resonance property of the resonant circuit 7 is checked in a stationary phase of the gas turbine (FIG. 5). The instantaneous actual value is recorded (method step 51) and checked using a desired value (method step 52). If the actual value deviates from the desired value to a tolerable extent, the ability of the heat shield 2 to function is still ensured. The length of any crack 5 which may be present has not yet reached a critical length. There is no need to replace the heat shield. On the other hand, if the actual value and desired value deviate from one another to an extent which cannot be tolerated, the ability of the heat shield to function is no longer ensured. The heat shield 2 needs to be replaced.

Figure 4:
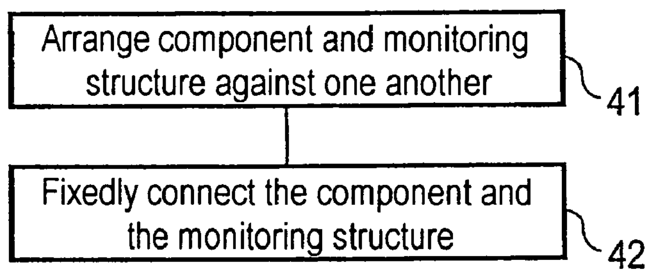
FIG. 4 shows a process for producing an arrangement comprising component and monitoring device.

To produce the arrangement 1, the heat shield 2 and the monitoring structure 4 are arranged against one another and are fixedly connected to one another (process steps 41 and 42, FIG. 4). For this purpose, an electrically conductive, ceramic paste is applied to the surface portion 10 of the heat shield 2 in the form of the monitoring structure 4 and is sintered together with the heat shield 2. During the sintering operation, the electrically conductive paste is consolidated to form the ceramic conductor.

EXAMPLE 2

Unlike in the arrangement described above, the monitoring structure 4 comprises a network of internal interconnects 14 and external interconnects 14. Each of the interconnects 14 and 15 is distinguished by a defined DC resistance. At those locations of the heat shield 2 which are not influenced by cracks 5, the interconnects 14 and 15, as electrical contact locations 16 for determining the electrical property of the monitoring structure, are routed as far as the edge of the heat shield 2. The internal interconnects 14 are not normally influenced by cracks 5. They are used to check the contact locations 16 during the determination of the DC resistance of the monitoring structure. For this purpose, the internal interconnects 14 have a different electrical resistance than the external interconnects 15.

The monitoring device 3 and the monitoring structure 4 are not permanently electrically connected to one another. An electrical connection (coupling) between monitoring device 3 and the monitoring structure 4 is briefly produced during the determination of an electrical parameter (DC resistance, impedance, capacitance, etc.).

In the event of a crack 5, there is an increase in the electrical DC resistance of the interconnect 15 which has been destroyed by the crack 5.

EXAMPLE 3

The arrangement described above is used to record degradation of the heat shield not by measuring the DC resistance of the monitoring structure 4, but rather by measuring the frequency-dependent impedance of the monitoring structure.

The invention claimed is:

1. An assembly comprising:

a ceramic heat shield deemed acceptable only in the absence of any crack propagating from an edge of the heat shield toward a center of the heat shield to a critical location of the heat shield, the heat shield deemed acceptable with cracks not extending to the critical location, a length of a crack extending from the edge to the crucial location defining critical length;

a monitoring structure applied to the heat shield and comprising a radiofrequency resonant circuit, the radiofrequency resonant circuit further comprising an electrical conductor attached to the heat shield at a distance equal to the critical length from the edge of the heat shield; and a monitoring device comprising an antenna adapted for remote wireless interrogation of the monitoring structure via radiofrequency excitation of the radiofrequency resonant circuit;

wherein a crack propagating from the edge of the heat shield toward the center of the heat shield exceeding the critical length will cause a crack in the electrical conductor, thereby changing a radiofrequency resonance of the radiofrequency resonant circuit that is remotely detectable by the monitoring device for identifying the heat shield as defective.

2. The assembly of claim 1, wherein the electrical conductor is formed in the shape of a ring around the center of the heat shield at the critical length distance from the edge, thereby enabling the monitoring structure to monitor an entire surface of the ceramic heat shield.

3. The assembly of claim 1, wherein the monitoring structure is applied to a surface of the heat shield that is not accessible in an installed state in a gas turbine engine.

4. An assembly comprising:

an electrical conductor applied to a surface of a component, the electrical conductor comprising a coil forming part of a radiofrequency resonant circuit and functioning as an antenna for receiving and responding to a radiofrequency interrogation of the resonant circuit; and a monitoring device comprising an antenna adapted for remotely conducting the radiofrequency interrogation of the resonant circuit without a need for physical access to the component surface;

wherein a crack propagating across the surface of the component will cause a break in the electrical conductor, thereby changing a resonance of the radiofrequency resonant circuit in response to the radiofrequency interrogation that is detectable by the monitoring device for identifying a degraded condition of the component.

5. The assembly of claim 4, wherein the electrical conductor is applied to the surface of the component generally parallel to a circumference of the surface so that an entire area of the surface is monitored for the degraded condition.

* * * * *